United States Patent
Rousselle et al.

(10) Patent No.: US 9,487,097 B2
(45) Date of Patent: *Nov. 8, 2016

(54) METHOD AND DEVICE FOR OPTIMIZED RECHARGING OF AN ELECTRIC BATTERY

(75) Inventors: Mélaine Rousselle, Vanves (FR); Gaizka Alberdi, Vanves (FR)

(73) Assignees: ELECTRICITE DE FRANCE, Paris (FR); ELECTRICITE RESEAU DISTRIBUTION FRANCE, Paris la Defense (FR)

( * ) Notice: Subject to any disclaimer, the term of this patent is extended or adjusted under 35 U.S.C. 154(b) by 112 days.

This patent is subject to a terminal disclaimer.

(21) Appl. No.: 14/343,209

(22) PCT Filed: Sep. 6, 2012

(86) PCT No.: PCT/FR2012/051990
§ 371 (c)(1),
(2), (4) Date: Mar. 6, 2014

(87) PCT Pub. No.: WO2013/034854
PCT Pub. Date: Mar. 14, 2013

(65) Prior Publication Data
US 2014/0217993 A1   Aug. 7, 2014

(30) Foreign Application Priority Data

Sep. 7, 2011  (FR) ..................... 11 57960

(51) Int. Cl.
*H02J 7/14*   (2006.01)
*H02J 7/04*   (2006.01)
(Continued)

(52) U.S. Cl.
CPC ........ *B60L 11/1809* (2013.01); *B60L 11/1825* (2013.01); *B60L 11/1844* (2013.01);
(Continued)

(58) Field of Classification Search
CPC ............... H02J 7/14; H02J 7/04; H02J 7/16; H02J 7/008; H02J 3/14; G01N 27/416; G08B 21/00; B60L 11/1809; B60L 11/1825; B60L 11/1844; B60L 2200/12; B60L 2230/40; B60L 2240/70; B60L 2240/80; Y02E 60/721; Y02T 10/7005; Y02T 10/7011; Y02T 10/7088; Y02T 10/7291; Y02T 90/121; Y02T 90/128; Y02T 90/14; Y02T 90/16; Y02T 90/163; Y02T 90/168; Y04S 10/126; Y04S 30/12
USPC ........................ 320/157, 132, 104; 307/429; 340/636.12, 636.16
See application file for complete search history.

(56) References Cited

U.S. PATENT DOCUMENTS 4,179,799 A * 12/1979 Fritts ...................... H01M 4/96
264/105

(Continued)

FOREIGN PATENT DOCUMENTS

EP   2 219 278 A1   8/2010
EP   2 355 294 A2   8/2011

OTHER PUBLICATIONS

Bashash et al., "Plug-in Hybrid Electric Vehicle Charge Pattern Optimization for Energy Cost and Battery Longevity," retrieved from internet website: http://faculty.ce.berkeley.edu/moura/pubs/JPS_ChgPatternOpt_Preprint.pdf; Journal of Power Sources, 196. 1, pp. 541-549 (2011).

(Continued)

*Primary Examiner* — Phallaka Kik
(74) *Attorney, Agent, or Firm* — Drinker Biddle & Reath LLP

(57) ABSTRACT

A method of optimized recharging of the electric battery of at least one electrical system by an electrical recharging device, in which the electric battery is recharged during at least one time interval by applying a charging power level associated with this time interval, this time interval belonging to an available charging time period initiated by the connecting of the recharging system of the electric battery to the electrical recharging device, and the charging power level being determined as a function of a charging curve associated with the electrical recharging device and of the residual electrical energy contained in the electric battery upon the connecting of the electric battery charging system to the electrical recharging device.

15 Claims, 5 Drawing Sheets

(51) Int. Cl.
| | |
|---|---|
| *H02J 7/16* | (2006.01) |
| *H02J 3/14* | (2006.01) |
| *G01N 27/416* | (2006.01) |
| *G08B 21/00* | (2006.01) |
| *B60L 11/18* | (2006.01) |
| *H02J 7/00* | (2006.01) |

(52) U.S. Cl.
CPC ............... *H02J 3/14* (2013.01); *H02J 7/008* (2013.01); *B60L 2200/12* (2013.01); *B60L 2230/40* (2013.01); *B60L 2240/70* (2013.01); *B60L 2240/80* (2013.01); *G01N 27/416* (2013.01); *G08B 21/00* (2013.01); *Y02E 60/721* (2013.01); *Y02T 10/7005* (2013.01); *Y02T 10/7011* (2013.01); *Y02T 10/7088* (2013.01); *Y02T 10/7291* (2013.01); *Y02T 90/121* (2013.01); *Y02T 90/128* (2013.01); *Y02T 90/14* (2013.01); *Y02T 90/16* (2013.01); *Y02T 90/163* (2013.01); *Y02T 90/168* (2013.01); *Y04S 10/126* (2013.01); *Y04S 30/12* (2013.01)

(56) References Cited

U.S. PATENT DOCUMENTS

| | | | | | |
|---|---|---|---|---|---|
| 5,032,825 | A | * | 7/1991 | Kuznicki | G08B 21/185 320/136 |
| 5,191,291 | A | * | 3/1993 | Taylor | G01R 31/3631 320/134 |
| 5,677,615 | A | * | 10/1997 | Takano | G01R 19/16542 320/152 |
| 6,046,574 | A | * | 4/2000 | Baranowski | G01R 19/16542 320/132 |
| 6,329,823 | B2 | * | 12/2001 | Blessing | G01N 27/416 320/136 |
| 6,388,447 | B1 | * | 5/2002 | Hall | H02J 7/0047 324/426 |
| 2001/0020849 | A1 | * | 9/2001 | Blessing | G01R 31/3624 324/426 |
| 2002/0195999 | A1 | * | 12/2002 | Kimura | G01R 31/3624 320/134 |
| 2008/0183408 | A1 | * | 7/2008 | Matsuura | G01R 31/3651 702/63 |
| 2009/0318834 | A1 | * | 12/2009 | Fujiwara | A61B 5/1411 600/583 |
| 2010/0168534 | A1 | * | 7/2010 | Matsumoto | A61B 5/14 600/309 |
| 2011/0156651 | A1 | | 6/2011 | Christensen | |
| 2014/0049109 | A1 | * | 2/2014 | Kearns | H02J 3/00 307/52 |
| 2014/0067151 | A1 | * | 3/2014 | Erhart | G05F 1/66 700/297 |
| 2014/0217979 | A1 | * | 8/2014 | Rousselle | B60L 11/1844 320/109 |

OTHER PUBLICATIONS

Caramanis et al., "Management of Electric Vehicle Charging to Mitigate Renewable Generation Intermittency and Distribution Network Congestion," Joint 48th IEEE Conference on Decision and Control and 28th Chinese Control Conference, Shanghai, P.R. China, pp. 4717-4722 (Dec. 16-18, 2009).

Clement-Nyns et al., "Analysis of the Impact of Plug-In Hybrid Electric Vehicles on Residential Distribution Grids by using Quadratic and Dynamic Programming," EVS International Battery, Hybrid and Fuel Cell Electric Vehicle Symposium, Stavanger, Norway, World Electric Vehicle Journal, vol. 3, pp. 1-11 (2009).

Pratt, "Energy Management Systems," Energy Management Systems Presentation for Urban Sustainability Symposium, retrieved from internet website: http://www.wilfredpinfold.com/blog/files/5_Pratt-Energy%20Management%20Systems%20presentation%20for%20Urban%20Sustainability%20Symposium.pdf , pp. 1-21.

Rousselle, "Impact of the Electric Vehicle on the Electric System," Master Thesis, EG201X, pp. 1-98, retrieved from internet website: http://www.ee.kth.se/php/modules/publications/reports/2009/XR-EE-ES_2009_018.pdf (Dec. 2009).

Sojoudi et al., "Optimal charging of plug-in hybrid electric vehicles in smart grids," Power and Energy Society General Meeting, 2011 IEEE, San Diego, CA, Abstract (Jul. 2011).

Sundstrom et al., "Optimization Methods to Plan the Charging of Electric Vehicle Fleets," International Journal on Communication, 1(2), pp. 1-6 (2010).

* cited by examiner

METHOD AND DEVICE FOR OPTIMIZED RECHARGING OF AN ELECTRIC BATTERY

CROSS-REFERENCE TO RELATED APPLICATIONS

This application is the U.S. national phase of the International Patent Application No. PCT/FR2012/051990 filed Sep. 6, 2012, which claims the benefit of French Application No. 11 57960 filed Sep. 7, 2011, the entire content of which is incorporated herein by reference.

FIELD

The invention relates to the field of managing the recharging of electric batteries, particularly the recharging of electric batteries of electric vehicles.

There are currently many electrical systems comprising a system for storing electrical energy, in particular a system consisting of one or more electric batteries and their associated recharging system, which can be connected to a electrical grid for recharging.

BACKGROUND

These electrical systems include electric vehicles having an electrical energy storage system which can be connected to power supply terminals by means of a recharging plug. The power supply terminals are each connected to the electrical grid.

Usually, charging the electric battery of such electrical systems begins the moment this battery is connected to the electrical grid and ends when this electric battery is disconnected from the electrical grid.

In the specific case of electric vehicles, the recharging begins the moment the recharging plug of the electric vehicle is plugged into the power supply terminal and continues as long as the electric vehicle is not unplugged, meaning until the user of the vehicle wishes to claim his vehicle or as long as the battery is not full.

This type of charging is not optimal, however, because the recharging does not consider constraints related to the grid, to the electric battery to be charged, or to the user of the electrical system to be recharged.

The constraints of the electrical grid to which the power supply terminal is connected can be expressed as the load curve of a transformer or of a delivery point, which is not uniform over time. For example, a transformer is stressed when its load exceeds its rated capacity.

The higher the load on the transformer, the more the transformer heats up, which accelerates its aging. In addition, large fluctuations in the load can result in sudden expansions and mechanical stresses. Ultimately, this transformer can grow louder due to the widening gaps.

As for the electric battery to be recharged, it can have widely varying charge levels when it is plugged into a power supply terminal, which determines the required amount of electrical energy to be obtained from the power supply terminal, and therefore the charging time required to reach a full charge.

Finally, concerning the constraints of the user of the electric recharging system, the user connects and disconnects the system at times which vary greatly depending on his schedule. When the electrical system is an electric car, the driver of the vehicle parks and reclaims his vehicle at times that depend on his schedule, which affects the available charging time of the power supply terminal.

SUMMARY

The present invention seeks to overcome the above disadvantages by proposing an optimized recharging method which takes into account both the constraints related to the electrical grid and those related to the user of the electrical system to be recharged, as well as constraints related to the electric battery to be recharged, and which better protects the recharging devices of the electrical grid.

For this purpose, it proposes a method for the optimized recharging of the electric battery of at least one electrical system by an electrical recharging device, wherein the electric battery is recharged during at least one time interval by applying a charging power level associated with this time interval, this time interval being within an available charging time period initiated by the connecting of the electric battery recharging system to the electrical recharging device, and the charging power level being determined as a function of a load curve associated with said electrical recharging device and of the residual electrical energy contained in the electric battery when the electric battery recharging system is connected to the recharging device.

In one embodiment, the method comprises the sampling of the load curve over an available charging time period in order to obtain a set of load curve power values respectively associated with consecutive time intervals, and sorting, in ascending order, the load curve power values in order to obtain a set of sorted load curve power values;

the electric battery of the electric vehicle being recharged during k charging time intervals respectively associated with the first k values of the sorted load curve power values, the charging power levels respectively applied during said k charging time intervals being determined as a function of the k+1 sorted load curve power value.

In one particularly advantageous embodiment, the determination of the charging power levels applied during said k charging time intervals comprises the following steps, executed while the index k, starting from an initial value of 1, is incremented:

associating, for the k time intervals associated with the k first values of the sorted load curve power values, a load curve power value at rank k that is equal to the k+1 sorted load curve power value;

calculating, for each of the k time intervals associated with the k first values of the sorted load curve power values, a charging power level at rank k associated with said time interval, the charging power level at rank k being determined as a function of the difference between the load curve power value at rank k and the load curve power value which are associated with the time interval;

comparing an electrical energy at rank k, determined by applying the charging power levels at rank k over the k time intervals with which they are respectively associated, with an electrical energy required to recharge the battery;

incrementing the index k if the electrical energy at rank k is less than or equal to the energy required to recharge the battery.

In one embodiment, for each of the k time intervals associated with the k first values of the sorted load curve power values, the charging power level at rank k associated with the time interval is equal to the minimum value between, on the one hand, a maximum load curve power value, and on the other hand, the difference between the load curve power value at rank k and the load curve power value which are associated with this time interval.

In another embodiment, when the electrical energy at rank k is greater than the energy required to recharge the battery, for each of the k time intervals associated with the k first values of the sorted load curve power values, the charging power level at rank k associated with this time interval is equal to the minimum value between, on the one hand, a maximum load curve power value, and on the other hand, the sum of the charging power level at rank k–1 and of the difference between the energy required and the electrical energy at rank k–1 divided by the number k.

In another embodiment, when the electrical energy at rank k is less than or equal to the energy required to recharge the battery, the determination further comprises a comparison between a charging duration at rank k, equal to the sum of the k time intervals associated with the k first values of the sorted load curve power values, and the duration of the available charging time period, the index k only being incremented if the charging duration at rank k is less than or equal to the duration of the available charging time period.

In particular, when the charging duration at rank k is greater than the duration of the available charging time period and when the electrical energy at rank k differs from the energy required to recharge the battery by at least a predetermined difference, the determination includes the calculation, for each consecutive time interval of the available time period, of a charging power level to be applied which is equal to the minimum value between, on the one hand, a maximum load curve power value, and on the other hand, the sum of the power level at rank k associated with said time interval and the difference between the electrical energy at rank k and the required energy divided by the number k.

In one particular embodiment, the recharging of the electric battery further comprises, for each of the charging time intervals with which a charging power level is associated, the comparison between a limit capacity level associated with this charging time interval and an estimated increased load curve power value equal to the sum of the load curve power value and of the charging power level which are associated with this charging time interval, the charging power level only being applied, during this charging time interval, if said estimated increased load curve power value is less than the limit capacity level associated with this charging time interval.

It is particularly advantageous if each charging time interval, for which the estimated increased load curve power value is greater than or equal to the limit capacity level associated with this charging time interval, is associated with a charging power value substantially equal to the difference between the limit capacity level and the load curve power value which are associated with this charging time interval.

In one embodiment, the available charging time period is determined as a function of the moment when the electric battery recharging system is connected to the electrical recharging device and of an indication concerning the charging end time provided by the user of the electric vehicle.

In another embodiment, the method comprises a prior verification of the available charging time period as a function of the length of time required for fully recharging the electric battery, the recharging of the electric battery during said at least one charging time interval only occurring if the duration of the available charging time period is greater than the length of time required for fully recharging the electric battery.

In one particular embodiment, the electric battery is able to be modulated in charging power and has substantially no memory effect, in particular a Lithium-Ion battery.

The present invention further provides a computer program comprising instructions for implementing the steps of the above method when it is executed by a processing unit of an electrical recharging system. Such a program is to be considered a product in the context of the protection sought by this patent application.

The present invention also provides an optimized recharging device for recharging at least one electric vehicle, connected to an electrical grid and comprising at least one connection port suitable for connection to the electric battery of an electric vehicle, the device being configured to implement the steps of the above method after the electric battery of an electric vehicle is connected to the connection port of the optimized recharging device.

Finally, the present invention proposes an optimized recharging system for recharging a fleet composed of at least one electric vehicle, the system comprising an electrical grid and at least one electrical recharging device as described above, connected to said electrical grid. In particular, this system further comprises a remote computer system, connected to the electrical recharging device and comprising a processing unit suitable for carrying out the steps of the above method.

BRIEF DESCRIPTION OF THE DRAWINGS

Other features and advantages of the invention will appear from the following detailed description and the accompanying drawings in which.

DETAILED DESCRIPTION

Figure 1:
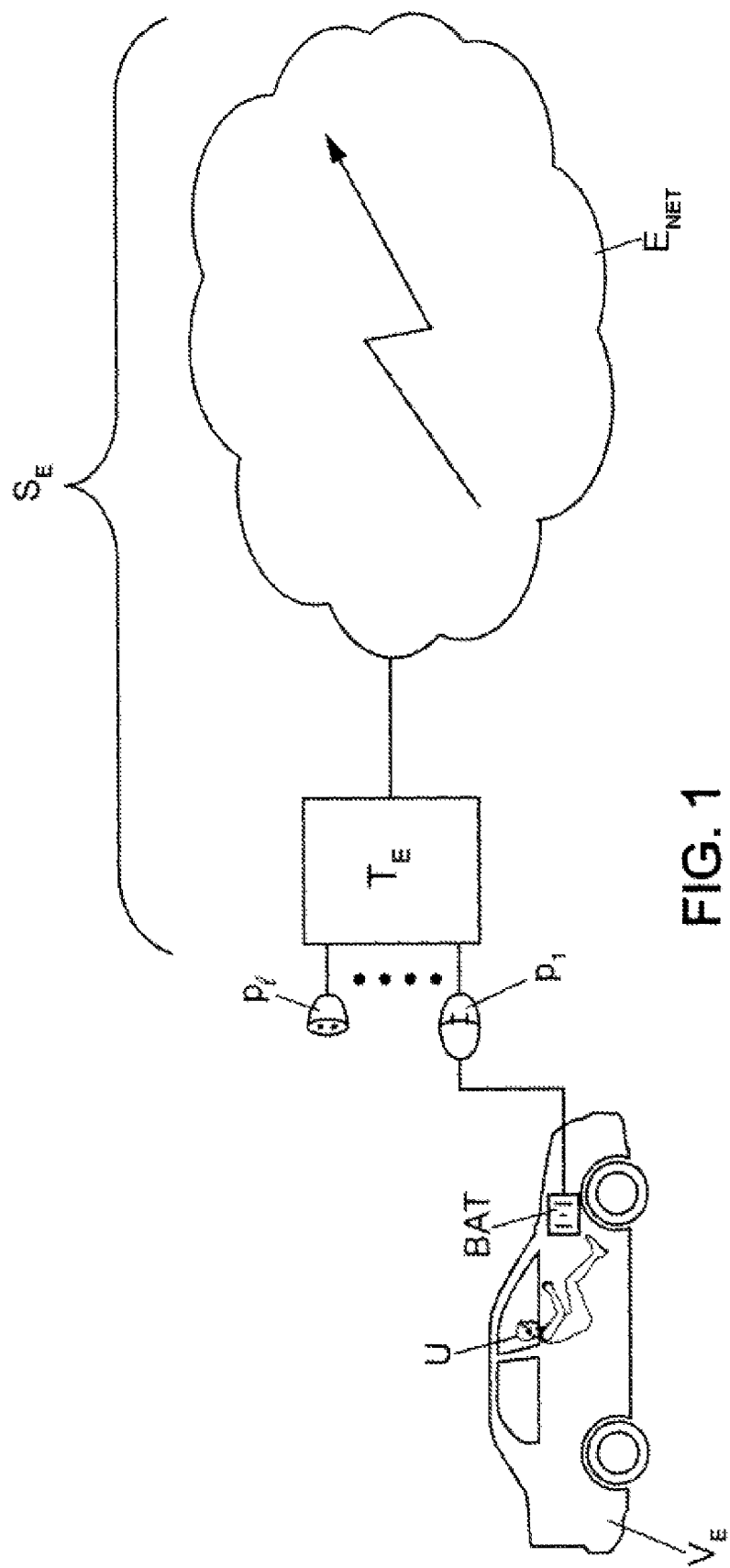
FIG. 1 illustrates an optimized system for recharging electric vehicles according to the present invention.

The following will first refer to FIG. 1, which illustrates an optimized system for recharging electric vehicles according to the present invention.

This optimized recharging system, designated by $S_E$ in FIG. 1, comprises at least one electrical recharging device $T_E$, suitable for connecting to the recharging system for the electric battery BAT of one or more electrical systems $V_E$ in order to recharge it.

A single electrical recharging device $T_E$ and a single electrical system $V_E$ are represented in FIG. 1, purely for illustrative purposes, but the optimized recharging system $S_E$ can include any number of electrical recharging devices in order to be able to recharge any number of electrical systems.

This electrical recharging device $T_E$ is itself connected to an electrical grid $E_{NET}$ where it obtains the electrical energy required for recharging and may comprise a power transformer, for example. The device $T_E$ thus has one or more connection ports $p_1, \ldots, p_l$ suitable for connecting to the electric battery BAT of an electrical system in order to recharge it using the electricity provided by the electrical grid $E_{NET}$.

The electrical system $V_E$ includes one or more electric batteries BAT associated with a battery recharging system. This electrical system $V_E$ is used by a user U who connects and disconnects the recharging system for this electric battery BAT to the electrical recharging device $T_E$, according to his schedule.

Purely for illustrative purposes, FIG. 1 represents the electrical system $V_E$ as an electric vehicle, as the present invention has particularly advantageous applications for this particular type of electrical system. In this illustrative example, the electric vehicle $V_E$ is driven by a user U who connects and disconnects the recharging system for the electric battery BAT to the electrical recharging device $T_E$ according to his schedule. Such an electric vehicle can be a car, a moped, or any other system having a battery that can be recharged from the electrical grid.

In the optimization of the electrical recharging system $V_E$, different constraints thus apply to the optimized recharging system described in FIG. 1:
  the constraints related to the recharging electrical grid, such as the load curve associated with the electrical recharging device $T_E$;
  the constraints related to the electric battery to be recharged, such as the charge profile of the electric battery BAT, or the electrical energy still stored in the battery when the user U plugs the battery BAT into the electrical recharging device $T_E$, and
  the constraints related to the user U himself, particularly his schedule, which affect the times when he connects and disconnects the electrical system to/from the electrical recharging device $T_E$, and therefore affects the available charging time for the battery BAT.

In the present invention, the electric battery BAT of the electrical system $V_E$ is recharged during at least one charging time interval $\Delta T_{chg}(i)$ within an available charging time period Td, which is initiated by connecting the recharging system for this electric battery BAT to the electrical recharging device $T_E$, which allows optimizing the recharging of this battery based on certain constraints related to the user's schedule.

The charging time interval $\Delta T_{chg}(i)$ is determined as a function of a load curve TLC associated with the electrical recharging device $T_E$, which also allows optimizing the charging of the electric battery BAT according to constraints related to the electrical recharging device $T_E$, and therefore to the optimized recharging system $S_E$.

Such a load curve TLC can be estimated at a given moment, for example on the basis of an expected load variation, or updated during charging so as to ensure ongoing load optimization according to the state of the electrical recharging device $T_E$ at that moment in time. By way of illustration, the load curve TLC may be estimated on the basis of predefined load curve models or load curve models calculated from a recorded history of loads on the electrical recharging device $T_E$. Updating the load curve TLC may be achieved through real-time sampling of the load on the electrical recharging device $T_E$. Such updating is particularly attractive in cases where a large number of batteries are connected and are recharging at the same time, which can lead to large variations in the load curve TLC.

Figure 2:
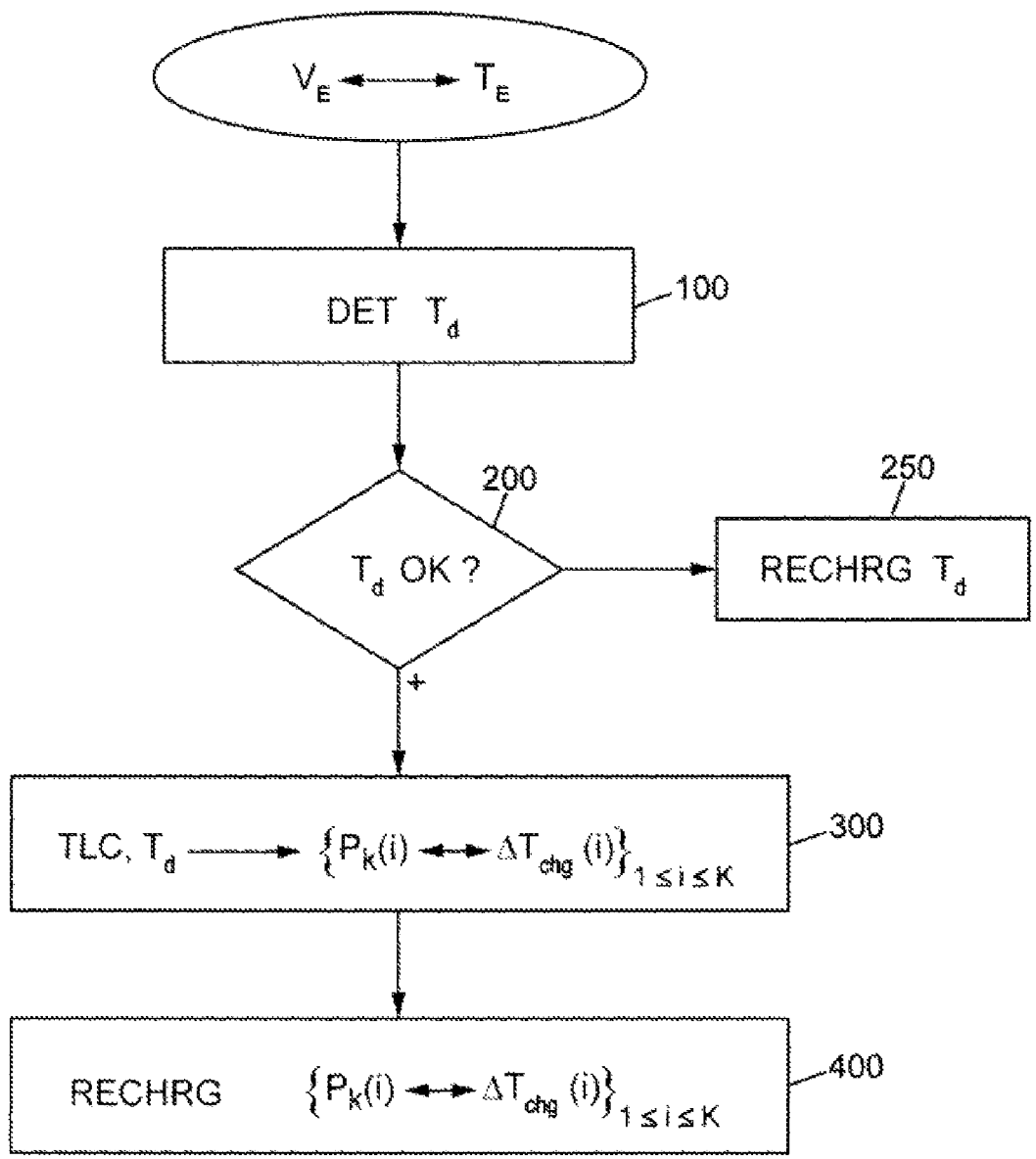
FIG. 2 illustrates the steps of an optimized method for recharging an electric vehicle according to the present invention.

We will now refer to FIG. 2, which illustrates the steps of an optimized method for recharging the electric battery of an electrical system according to the present invention.

This method concerns the optimized recharging of the electric battery of one or more electrical systems $V_E$ by an electrical recharging device $T_E$, the electrical system $V_E$ comprising an electric battery BAT associated with a recharging system that can be connected to this electrical recharging device $T_E$ in order to perform this recharging. The optimized recharging of a single electrical system $V_E$ is described below for illustrative purposes, but the method can be applied to the recharging of any number of electrical systems.

This method may first include the determination (step 100) of an available charging time period Td, performed to take user constraints into account, especially his schedule, which influences the time available for recharging the electric battery BAT.

Thus, the moment $t_A$ when the electric battery BAT recharging system is connected to the electrical recharging device $T_E$ allows determining the start of the available charging time period Td. In other words, this moment $t_A$ when the electric battery is connected begins the available charging time period Td.

To determine the moment $t_D$ corresponding to the end of the available charging time period Td, it is advantageous to ask the user to indicate the time he plans to disconnect the electrical system $V_E$ (for example the time he expects to reclaim his electric vehicle), for example the time he anticipates leaving for work in the morning. The user U can provide an indication concerning this charging end time $t_D$, for example via a dedicated web interface on a smartphone or on the dashboard of the electric vehicle used.

Once this available charging time period Td is determined, it is advantageous to verify beforehand (step 200) that the available charging time period Td is sufficient, so that the optimized recharging process is only begun if such is the case. Otherwise, a conventional recharging process can be implemented (step 250) for the entire duration of the available charging time period Td, as will be explained below.

Figure 3:
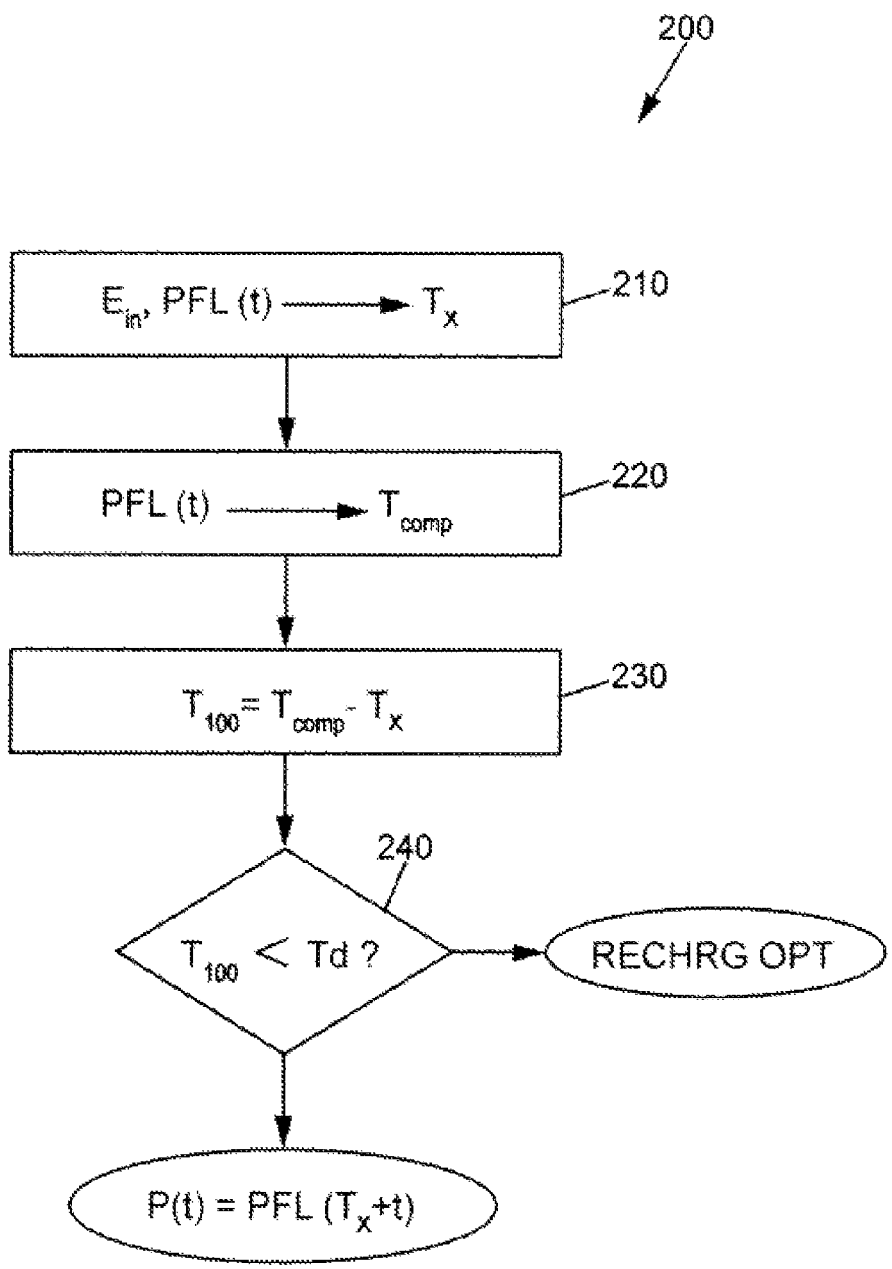
FIG. 3 illustrates an implementation of a pre-verification step of the optimized recharging method according to the present invention.

FIG. 3 illustrates one embodiment of such a pre-verification step 200.

In this embodiment, a partial charging period Tx is first calculated (step 210), corresponding to the level of residual electrical energy $E_{in}$ remaining in the electric battery BAT when it is connected to the recharging device $T_E$.

In other words, this partial charging period Tx corresponds to the time needed to recharge the electric battery BAT from a state where it is empty of energy (a zero state of charge SoC) to the level of residual electrical energy $E_{in}$.

Figure 4:
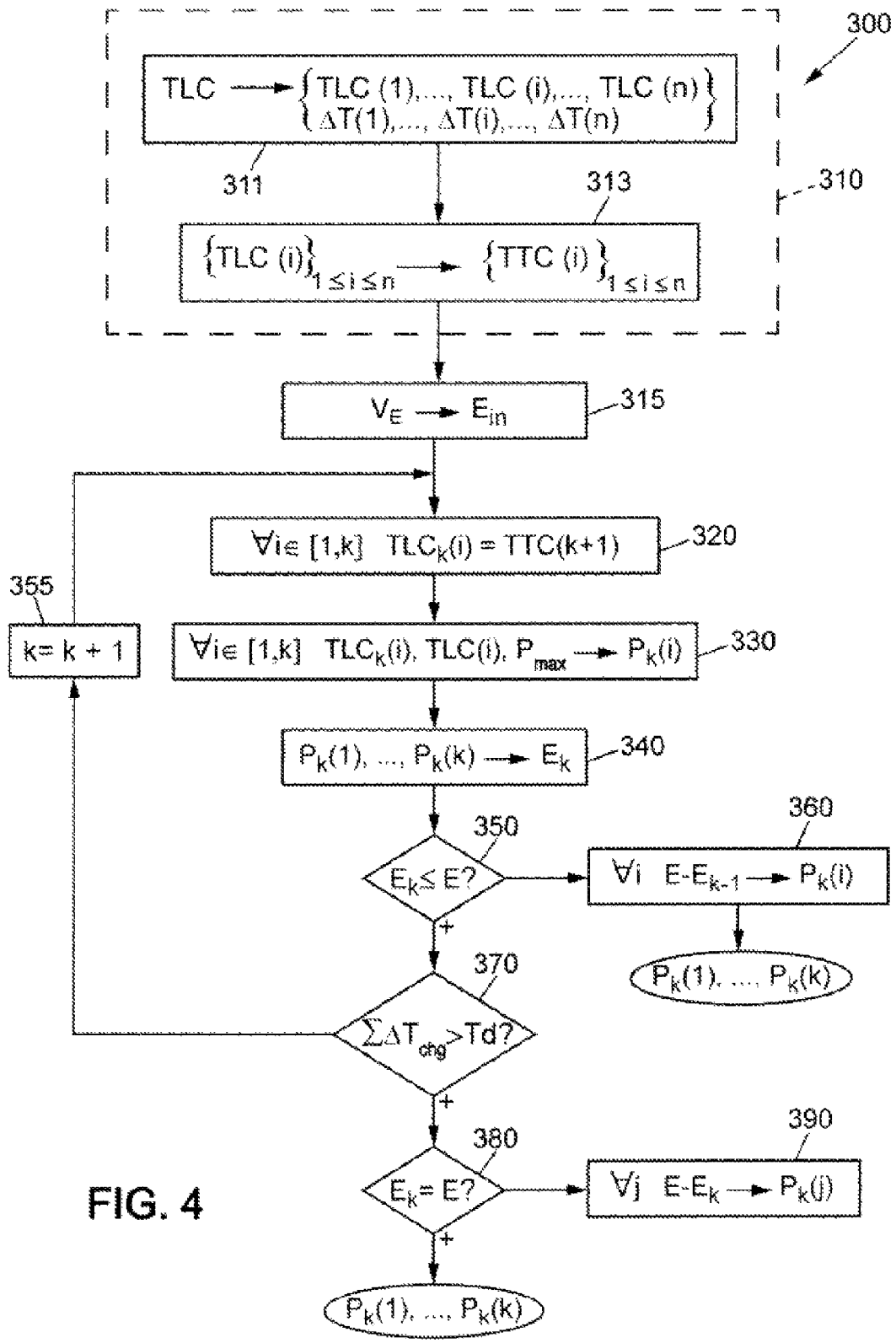
FIG. 4 illustrates an implementation of the step of determining the power levels to be applied in the optimized recharging method according to the present invention.

In the particular case where the information available at the time of connection consists of a state of charge $SoC_0$ of the battery BAT, this level of residual electrical energy $E_{in}$ is calculated beforehand using the following equation (1):

$$E_{in} = E_{expl} \cdot SoC_0 \qquad (1)$$

where:

$E_{expl}$ is the usable capacity of this battery BAT; and $SoC_0$ is the state of charge of the electric battery BAT at the time it is connected to the recharging device $T_E$ (meaning at time $t_A$ illustrated in FIG. 4).

The partial charging period Tx is then determined using the following equation (2):

$$E_{in} = \eta_{BAT} \cdot \eta_{chrgr} \int_0^{Tx} PFL(t)dt, \qquad (2)$$

where:

$\eta_{BAT}$ is the efficiency parameter for the battery BAT, between 0 and 100%;

$\eta_{chrgr}$ is the efficiency parameter for the charger for this battery BAT, also between 0 and 100%; and PFL(t) is the charge profile for the battery BAT pulling from the electrical grid.

The complete charging period Tcomp, corresponding to the time required for fully recharging the electric battery BAT from an empty state (a zero state of charge SoC) is then determined (step 220) based on the charge profile PFL(t) of the electric battery BAT.

In particular, this charging period Tcomp is calculated using the following equation (3):

$$E_{max} = \eta_{BAT} \cdot \eta_{chrgr} \int_0^{Tcomp} PFL(t) dt \qquad (3)$$

where $E_{max}$ is the level of electrical energy reached at the end of this full recharge, typically corresponding to the maximum charge level of the electric battery BAT. However, the invention is not limited to this case, and can also be applied to the case where $E_{max}$ is a level of electrical energy corresponding to a specific charge level that is different from the maximum charge level of the electric battery BAT.

The steps of determining 210 the partial charging period Tx and determining 220 the complete charging period Tcomp are not necessarily performed in the order indicated above, but may very well be performed in the reverse order, meaning with the determination of the complete charging period Tcomp preceding the determination of the partial charging period Tx.

Once the durations Tx and Tcomp have been determined, the charging duration $T_{100}$ necessary to achieve a full charge of the battery BAT containing residual energy $E_{in}$ can be determined (step 230) using the following equation:

$$T_{100} = Tcomp - Tx \qquad (4)$$

This duration $T_{100}$ can then be compared (step 240) to the duration of the available charging time period Td, to determine whether there is enough time to complete a full charge.

If this duration $T_{100}$ is less than the duration of the available charging time period Td, then it is advantageously possible to apply the optimized recharging method according to the present invention. On the other hand, if this duration $T_{100}$ is greater than the duration of the available charging time period Td, then a full recharging of the electric battery BAT is not possible.

In the latter case, a conventional recharging can be performed in which the charge profile PFL(t), shortened by duration Tx, is applied during the entire available charging time period Td, meaning where the charging schedule during this period Td is based on a charging power corresponding to P(t)=PFL(Tx+t).

To return to the optimized recharging method shown in FIG. 2, after having determined the available charging time period Td and optionally after having verified that duration $T_{100}$ is smaller than the duration of this available charging time period Td, one or more charging power levels $P_k(i)$ to be respectively applied during one or more charging time intervals $\Delta T_{chg}(i)$ within the available charging time period Td, initiated by the connection of the electric battery BAT recharging system to the electrical recharging device $T_E$, are then determined (step 300), a charging power level $P_k(i)$ being determined for each charging time interval $\Delta T_{chg}(i)$ and associated with said charging time interval.

The determination of the charging power level(s) $P_k(i)$ is performed as a function of a load curve TLC associated with the electrical recharging device $T_E$ and as a function of the residual electrical energy $E_{in}$ contained in the electric battery BAT when the electric battery is connected to the electrical recharging device.

The electric battery BAT is then recharged (step 400) during the charging time interval(s) $\Delta T_{chg}(i)$ by applying, during each charging time interval $\Delta T_{chg}(i)$, the charging power level $P_k(i)$ associated with it.

Thus the recharging of the electric battery BAT occurs while taking into account constraints of the user (reflected by the available charging time period Td), of the electrical grid (reflected by the load curve TLC of the electrical recharging device $T_E$), and of the electric vehicle (reflected by the residual electrical energy $E_{in}$ still contained in the electric battery BAT at the time it is connected to the electrical recharging device $T_E$).

FIG. 4 illustrates an implementation of the step 300 of determining the power levels to be applied.

This determination step comprises the prior determination (step 310) of a set $\{TLC(i)\}_{1 \leq i \leq n}$ of load curve power values sorted in ascending order based on the load curve TLC associated with the electrical recharging device $T_E$.

In particular, this prior determination step may first comprise the sampling (sub-step 311) of the load curve TLC associated with the electrical recharging device $T_E$, over the available charging time period Td, in order to obtain a set $\{TLC(i)\}_{1 \leq i \leq n}$ of load curve power values TLC(1) to TLC(n) each associated with consecutive time intervals $\Delta T(1)$ to $\Delta T(n)$ within the available charging time period Td.

This sampling is preferably periodic, at predetermined intervals corresponding to the duration of a charging time interval $\Delta T$. A load curve power value TLC(i) is then associated with the time index i indicating the $i^{th}$ time interval $\Delta T(i)$ contained within the available charging time period Td.

At the end of this sampling phase, load curve power values TLC(1), ..., TLC(i), ..., TLC(n) are respectively associated with a succession of consecutive time intervals $\Delta T(1)$, ..., $\Delta T(i)$, ..., $\Delta T(n)$ which are themselves designated by a succession of time indexes 1, ..., i, ... n, satisfying the relation $\Delta T(i) = i * \Delta T$.

This sampling of the load curve TLC makes it possible to work in discrete time, especially when sorting the indexes associated with the load curve power values, which is more easily achieved using computerized means.

Once the load curve TLC is sampled, the load curve power values TLC(1) to TLC(n) are then sorted (sub-step 313) in ascending order so as to obtain a set $\{TTC(i)\}_{1 \leq i \leq n}$ of sorted load curve power values, each of these sorted load curve power values $\{TTC(i)\}_{1 \leq i \leq n}$ being respectively associated with one of said time intervals $\Delta T(1)$ to $\Delta T(n)$.

Purely by way of example, if the following values TLC(i) are obtained by sampling the load curve every hour between 1 a.m. and 7 a.m.:

TLC(1)=75 kW
TLC(2)=80 kW
TLC(3)=70 kW
TLC(4)=65 kW
TLC(5)=65 kW
TLC(6)=60 kW
TLC(7)=70 kW the following sorted load curve power values TTC(i) are obtained:

TTC(1)=TLC(6)=60 kW;
TTC(2)=TLC(4)=65 kW;
TTC(3)=TLC(5)=65 kW;
TTC(4)=TLC(3)=70 kW;
TTC(5)=TLC(7)=70 kW;
TTC(6)=TLC(1)=75 kW; and
TTC(7)=TLC(2)=80 kW.

In this sort, when several load curve power values TLC(i) are identical, they can be sorted for example in chronological order, which is illustrated above with the values TLC(4) and TLC(5) which respectively give the sorted load curve power values TTC(2) and TTC(3).

Once the sorted load curve power values TTC(1) to TTC(n) are obtained, the residual electrical energy $E_{in}$ in the electric battery BAT of the electric vehicle is then determined (step 315).

This residual electrical energy $E_{in}$ is communicated as such by the electric vehicle $V_E$, if said vehicle is capable of measuring it. If, however, the electric vehicle $V_E$ measures the residual state of charge $SoC_0$ of the battery BAT at the time it is connected to the electrical recharging device $T_E$, then the residual electrical energy $E_{in}$ can be calculated based on this residual state of charge $SoC_0$ using the above equation (1).

Once the sorted load curve power values TTC(1) to TTC(n) and the residual electrical energy $E_{in}$ of the battery BAT are obtained, the charging power level(s) $P_k(i)$, to be applied during one or more charging time intervals among the consecutive time intervals $\Delta T(i)$, are then determined using these parameters.

In particular, at least a first charging power level $P_k(1)$ is applied during a first charging time interval $\Delta T_{chg}(1)$ corresponding to the time interval $\Delta T(i)$ associated with the first value TTC(1) of the sorted load curve power values, this first charging power level being determined as a function of the second value TTC(2) of the sorted load curve power values, in order to be able to raise this first charging power level.

More generally, k charging power levels $P_k(1), \ldots, P_k(k)$ are respectively applied during the k time intervals associated with the k first values TTC(1) to TTC(k) of the sorted load curve power values, these k charging power levels $P_k(1), \ldots, P_k(k)$ being determined as a function of the k+1 sorted load curve power value TTC(k), which allows raising the charging power levels of the battery BAT in the areas of low load in the load curve TLC of the electrical recharging device $T_E$.

Raising the charging power levels of the battery at these moments limits the impact of the electrical recharging device $T_E$ on the load curve TLC and avoids the negative effects associated with the areas of high load in this load curve TLC.

In the embodiment illustrated in FIG. 4, the determination of the k charging power levels $P_k(1), \ldots, P_k(k)$ which are applied during said k time intervals associated with the k first values TTC(1) to TTC(k) of the sorted load curve power values, comprises an iterative process that is a function of the index k, said index having an initial value of 1 and being incremented as long as certain conditions are not satisfied.

This iterative process comprises the following steps, repeated when the index k is incremented:

Each of the k time intervals associated with the k first values TTC(1), ..., TTC(i), ..., TTC(k) of the sorted load curve power values is associated (step 320) with a load curve power value at rank k, denoted by $TLC_k(i)$ for the time interval associated with the $i^{th}$ value TTC(i) of the sorted load curve power values, equal to the k−1 sorted load curve power value TTC(k+1).

For this operation, for all the time intervals associated with the k first values TTC(1), ..., TTC(i), ..., TTC(k) of the sorted load curve power values, the load curve power values at rank k $TLC_k(i)$ are raised to the level of the k+1 sorted load curve power value TTC(k+1).

Next, for each of the k time intervals associated with the k first values TTC(1), ..., TTC(i), ..., TTC(k) of the sorted load curve power values, a charging power level at rank k is calculated (step 330), denoted by $P_k(i)$ when this level is associated with the time interval itself associated with the $i^{th}$ sorted load curve power value TTC(i).

Here, for a time interval associated with the $i^{th}$ sorted load curve power value TTC(i), the charging power level at rank k $P_k(i)$ is determined as a function of the difference between the load curve power value at rank k $TLC_k(i)$ and the load curve power value TLC(i) which are associated with this time interval.

In one advantageous embodiment, for each of the k time intervals associated with the k first values TTC(1), ..., TTC(i), ..., TTC(k) of the sorted load curve power values, the charging power level $P_k(i)$ at rank k associated with this time interval is equal to the minimum value between, on the one hand, a maximum load curve power value $P_{max}$, and on the other hand, the difference between the load curve power value at rank k $TLC_k(i)$ and the load curve power value TLC(i) which are associated with this time interval.

In other words, the charging power level $P_k(i)$ at rank k is calculated using the following equation (5):

$$P_k(i) = \min(P_{max}, TLC_k(i) - TLC(i)) \quad (5)$$

The maximum load curve power value $P_{max}$ is a parameter that is dependent on the battery or on the contracted power.

Thus, in this advantageous embodiment, the power level $P_k(i)$ is always at most equal to this maximum load curve power value $P_{max}$, which guarantees that this threshold is never exceeded.

An electrical energy at rank k, denoted $E_k$, is then determined (step 340) by applying the charging power levels at rank k $P_k(i)$ over the k time intervals $\Delta T_{chg}(1), \ldots, \Delta T_{chg}(k)$ with which they are respectively associated.

This energy $E_k$ corresponds to the increase in electrical energy which can be obtained by raising the k first values of the sorted load curve power values.

In particular, this energy $E_k$ can be obtained by using the following equation (6):

$$E_k = \sum_{i=1}^{k} P_k(i) \cdot \Delta T_{chg}(i) \quad (6)$$

The electrical energy $E_k$ at rank k determined in this manner is then compared (step 350) with the electrical energy E required to recharge the electric battery BAT.

Such required electrical energy E can be defined beforehand. In particular, it can be defined as being the energy necessary for fully recharging the electric battery BAT. In this case it is dependent on the residual electrical energy $E_{in}$ contained in the electric battery when the electric battery is connected to the electrical recharging device. More specifically, it is equal to the difference between the maximum charge level $E_{max}$ of the electric battery and the residual electrical energy $E_{in}$ contained in the electric battery when the electric battery is connected to the electrical recharging device.

The index k is then incremented (step 355) if the electrical energy $E_k$ at rank k is less than or equal to the energy E required to recharge the battery.

If, on the other hand, the electrical energy $E_k$ at rank k is greater than the energy E required to recharge the battery, the index k is not incremented and the iterative process for obtaining the charging power levels to be applied stops at this point.

In a first embodiment, the charging power levels $P_k(1)$ to $P_k(k)$ obtained to this point can then be respectively applied during the time intervals $\Delta T_{chg}(1)$ to $\Delta T_{chg}(k)$ with which they are associated.

However, in another advantageous embodiment, for each of the k time intervals associated with the k first values $TTC(1), \ldots, TTC(i), \ldots, TTC(k)$ of the sorted load curve power values, the charging power level at rank k $P_k(i)$ associated with the time interval can be calculated (step 360) to be equal to the minimum value between, on the one hand, the maximum load curve power value $P_{max}$ defined above, and on the other hand, the sum of the charging power level at rank k−1 $P_{k-1}(i)$ associated with the time interval and of the difference between the required electrical energy E and the electrical energy at rank k−1 $E_{k-1}$, divided by the number k.

In other words, for the $i^{th}$ time interval concerned, the charging power level at rank k $P_k(i)$ is calculated using the following equation (7):

$$P_k(i) = \min\left(P_{max}, P_{k-1}(i) + \frac{E - E_{k-1}}{k}\right) \quad (7)$$

This operation allows equitably distributing, over the time intervals associated with the k first values $TTC(1), \ldots, TTC(i), \ldots, TTC(k)$ of the sorted load curve power values, the extra energy necessary between the electrical energy at rank k−1 $E_{k-1}$ and the required electrical energy E.

To this point, only one condition related to the comparison of the electrical energy at rank k $E_k$ with the energy E required to recharge the battery has been mentioned for deciding whether or not to continue the iterative process. However, it may be advantageous to add additional conditions.

In one advantageous embodiment, when the electrical energy at rank k $E_k$ is less than or equal to the energy E required to recharge the battery BAT, the determination process 300 may further comprise the comparison (step 370) of a charging duration at rank k, denoted by $\Sigma\Delta T_{chg}$, with the duration of the available charging time period Td. More specifically, the charging duration $\Sigma\Delta T_{chg}$ at rank k is equal to the sum of the k time intervals associated with the k first values of the sorted load curve power values.

In particular, when the time intervals $\Delta T(i)$ and the charging time intervals $\Delta T_{chg}(i)$ have a duration $\Delta T$ corresponding to the predetermined interval between periodic samplings, this means comparing the index k with the number n of consecutive time intervals $\Delta T(i)$.

The k is then only incremented if the charging duration $\Sigma\Delta T_{chg}$ at rank k is less than or equal to the duration of the available charging time period Td (in other words if the index k is less than the number n in the case of periodic sampling every $\Delta T$), meaning if the duration of the available charging period is sufficient to allow applying the k power levels $P_k(i)$ determined to that point over their k respective time intervals.

If such is not the case, meaning if the total duration of the k time intervals associated with the k first values TTC(1) to TTC(k) of the sorted load curve capacity values exceeds the duration of the available charging period Td (in other words if the index k is greater than or equal to the number n in the case of periodic sampling every $\Delta T$), then the iterative process stops at this point, the charging power to be applied to the electric battery BAT being modulated over the entire available charging period Td.

In one embodiment, the charging power levels $P_k(1)$ to $P_k(k)$ obtained to this point can then be respectively applied during the time intervals $\Delta T_{chg}(1)$ to $\Delta T_{chg}(k)$ with which they are respectively associated.

However, in another embodiment, it may be advantageous at this point to again compare (step 380) the electrical energy at rank k $E_k$ to the energy E required to recharge the electric battery BAT, in order to determine whether this electrical energy at rank k $E_k$ is different from the energy E required to recharge the electric battery BAT by at least a predetermined difference.

If the electrical energy at rank k $E_k$ does not substantially differ from the energy E required to recharge the electric battery BAT, then the charging power levels $P_k(1)$ to $P_k(k)$ obtained to this point can then be respectively applied during the time intervals $\Delta T_{chg}(1)$ to $\Delta T_{chg}(k)$ with which they are respectively associated.

Conversely, if the electrical energy at rank k $E_k$ differs from the energy E required to recharge the electric battery BAT by at least a predetermined difference, then, for each consecutive time interval $\Delta T(j)$ of the available time period Td, a charging power level is calculated (step 390) to be applied as a function of the power level at rank k $P_k(j)$ associated with this time interval and of the difference between the electrical energy at rank k $E_k$ and the energy E required.

More particularly, for each of the consecutive time intervals $\Delta T(j)$, the charging power level to be applied is equal to the minimum value between, on the one hand, a maximum load curve power value $P_{max}$, and on the other hand, the sum of the power level at rank k $P_k(j)$ associated with said time interval and the difference between the electrical energy at rank k $E_k$ and the energy E required divided by the number k.

In other words, for the $j^{th}$ time interval concerned, the charging power level at rank k $P_k(j)$ is calculated using the following equation (8):

$$P_k(j) = \min\left(P_{max}, P_k(j) + \frac{E - E_k}{k}\right) \quad (8)$$

At the end of this iterative process, a certain number k of charging power levels $P_k(1)$ to $P_k(k)$ are thus applied during k charging time intervals $\Delta T_{chg}(1)$ to $\Delta T_{chg}(k)$ corresponding to the k first values TTC(1) to TTC(k) of the sorted load curve power values, these k charging time intervals $\Delta T_{chg}(1)$ to $\Delta T_{chg}(k)$ possibly covering the entire available charging period Td if said period is relatively short compared to the amount of electrical energy to be recharged.

In one particular embodiment, the charging power levels $P_k(i)$ can be prevented from exceeding a limit capacity level $P_{lim}$ which can advantageously be fixed for example at 50-60% of the rated load capacity of the electrical recharging device $T_E$, with load levels exceeding this value being considered unfavorable.

This limit capacity value $P_{lim}$ may be constant over the entire available charging period or may have variations, in which case a limit capacity value $P_{lim}(i)$ is associated with each time interval $\Delta T(i)$, the values $P_{lim}(i)$ possibly being different from each other.

In this embodiment, after having determined the k charging power levels $P_k(1)$ to $P_k(k)$, a comparison is performed, for each of the time intervals $\Delta T_{chg}(i)$ having an associated charging power level $P_k(i)$, between the limit capacity level $P_{lim}(i)$ associated with the time interval $\Delta T_{chg}(i)$ and an estimated increased load curve power value, denoted by TLC+VE(i), corresponding to the sum of the load curve power value TLC(i) associated with time interval $\Delta T_{chg}(i)$ and of the charging power level $P_k(i)$ associated with time interval $\Delta T_{chg}(i)$.

The recharging during time interval $\Delta T_{chg}(i)$, at charging power level $P_k(i)$, only occurs if the estimated increased load curve power value TLC+VE(i) associated with this time interval $\Delta T_{chg}(i)$ is less than the limit capacity level $P_{lim}(i)$, in other words if the load curve is not increased beyond this limit capacity level $P_{lim}(i)$ by applying the optimized recharging method of the invention.

Conversely, if the estimated increased load curve power value TLC+VE(i) associated with this time interval $\Delta T_{chg}(i)$ is greater than or equal to the limit capacity level $P_{lim}(i)$, then the charging power level $P_k(i)$ as determined is not applied. In one embodiment, recharging is then disabled during this time interval $\Delta T_{chg}(i)$. In another more advantageous embodiment, the charging power value $P_k(i)$ is then recalculated so as to be substantially equal to the difference between the limit capacity level $P_{lim}(i)$ and the load curve power value TLC(i) which are associated with the time interval $\Delta T_{chg}(i)$.

In particular, in a case where it is acceptable for the increased load curve value TLC+VE(i) to reach the limit capacity level $P_{lim}(i)$, then the charging power value $P_k(i)$ can be equal to the difference between the limit capacity level $P_{lim}(i)$ and the load curve power value TLC(i) which are associated with the time interval $\Delta T_{chg}(i)$.

Conversely, if it is not acceptable for the increased load curve value TLC+VE(i) to reach the limit capacity level $P_{lim}(i)$, then the charging power value $P_k(i)$ can be equal to the difference between the limit capacity level $P_{lim}(i)$ and the load curve power value TLC(i) which are associated with the time interval $\Delta T_{chg}(i)$, reduced by a small predetermined power difference (for example about 1 KW), so that the increased load curve value nearly reaches, but does not equal and does not exceed, the limit capacity level $P_{lim}(i)$.

By thus preventing the recharging of the electric battery BAT within the areas of the load curve TLC that are greater than the limit capacity level $P_{lim}$, this embodiment protects the electrical recharging device $T_E$, although with a possibly incomplete recharging of the electric battery BAT.

Figure 5:
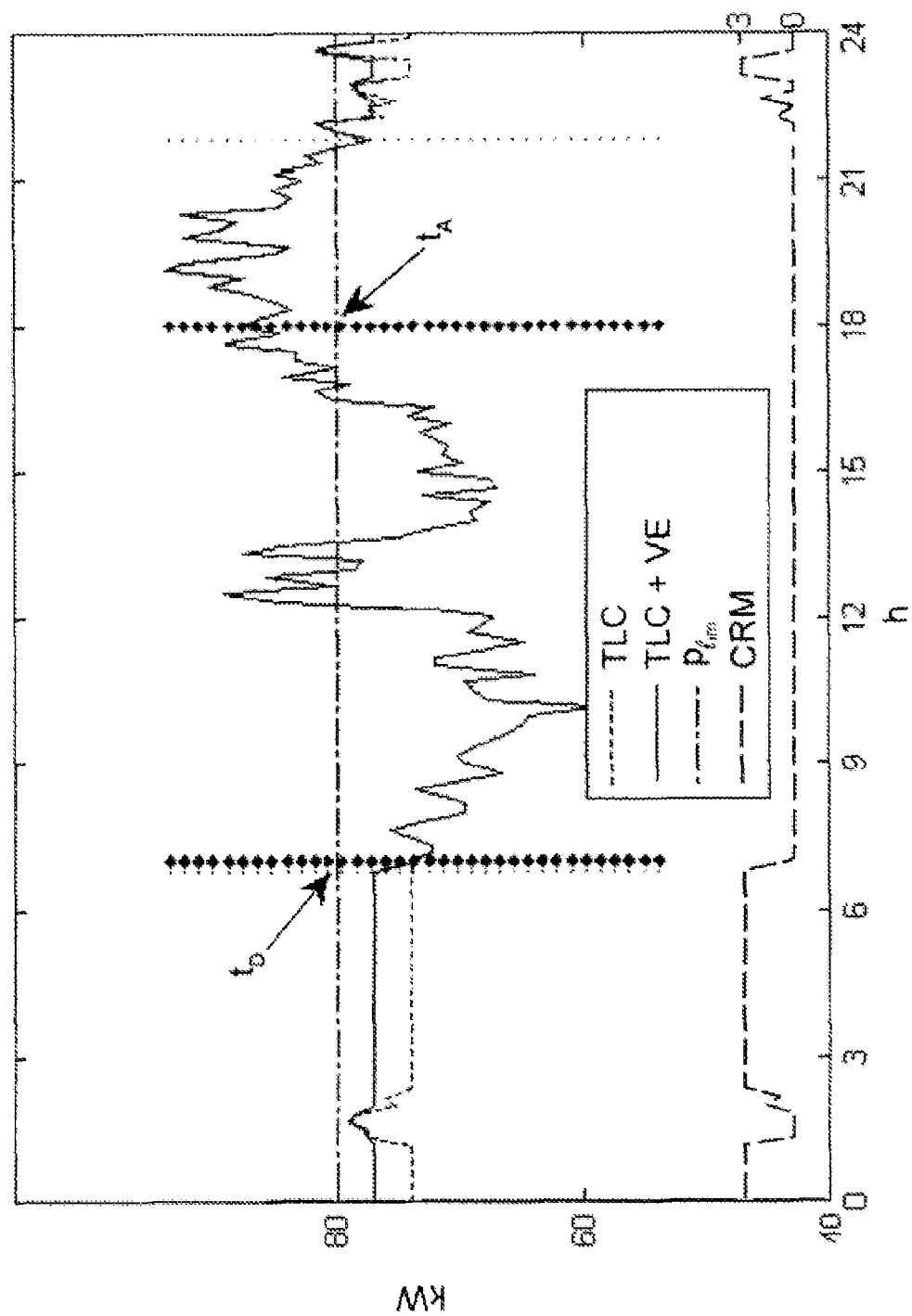
FIG. 5 represents a graph illustrating the positive effect obtained by using the optimized recharging method of the invention.

FIG. 5 is a graph showing the positive effect obtained when using the optimized recharging method of the invention.

This graph illustrates the load curve TLC for a transformer over the course of an entire day, as well as the curve representing the change over time of the limit capacity $P_{lim}$ beyond which the load curve TLC causes harmful effects, the limit capacity level $P_{lim}$ being defined here as 80 kW.

The time of arrival $t_A$ of the user at 6 p.m. (i.e. the moment when an electric vehicle $V_E$ is connected to the transformer) and the time of departure $t_D$ of the user at about 7 a.m. (i.e. the moment when the electric vehicle $V_E$ is disconnected from the supply terminal) are indicated, defining an available charging period Td that is equivalent to the interval $[t_A;t_D]$.

At the bottom of this graph one can see the curve CRM representing the variation over time of the charging power applied to the electric battery BAT.

It is particularly apparent in this curve CRM that the charging power applied to the electric battery BAT is primarily at its maximum at the moments where the load curve TLC is at its minimum or is at least below the limit capacity level $P_{lim}$.

The resulting load curve, designated by TLC+VE, is illustrated as well. It is clear from this resulting load curve that it is mainly the low points in the load curve TLC, located below the limit capacity level $P_{lim}$, which are raised by the optimized recharging of the vehicle $V_E$, and this occurs to a load value distributed along the entire available charging period Td. The load curve TLC is therefore smoothed by the method of the invention.

As a result, the increase in the load curve induced by recharging the vehicle $V_E$ is primarily confined to the minimal load values in the load curve TLC, which limits the negative effects on the transformer, unlike the case where charging is continuously enabled throughout the period $[t_A;t_D]$. With the present invention, power consumption due to charging is limited to only what is necessary for recharging the electric battery, without a continuous consumption of power necessarily occurring.

The different steps of the optimized recharging method described above can be implemented by a program suitable for execution by a processing unit of an optimized recharging system, for example implemented as a computer or a data processor, said program comprising instructions for controlling the execution of the steps of a method as mentioned above.

In particular, the processing unit in question may be located within the optimized recharging device $T_E$ or within the electrical system $V_E$, in order to locally manage the recharging of the electric vehicles.

Or the processing unit in question may be located remotely from the optimized recharging device $T_E$, in a remote computer system that is part of the optimized recharging system $S_E$, in order to manage the recharging centrally, which is appropriate in the case of a large fleet. In such a case, instructions are communicated to the optimized recharging device $T_E$ or to the electrical system $V_E$ via various telecommunication networks in order to manage the optimized recharging.

As for the program, it can use any programming language, and may be in the form of source code, object code, or intermediate code between source code and object code, such as in a partially compiled form, or in any other desirable form.

The invention also concerns a medium readable by a computer or data processor, and containing the instructions of a program as mentioned above. This medium may be any entity or device capable of storing the program. For example, the medium may consist of a storage medium such as a ROM, for example a CD-ROM or a microelectronic circuit ROM, or a magnetic recording medium such as a diskette or hard disk.

On the other hand, the medium may be a transmissible medium such as an electrical, optical, or electromagnetic signal, which may be conveyed via electrical or optical cable, by radio, or by other means. The program according to the invention may in particular be downloaded over a network such as the Internet. Alternatively, the medium may be an integrated circuit incorporating the program, the circuit being adapted to execute or to be used in executing the method in question.

The optimized recharging method of the invention is particularly advantageous for applications involving the recharging of electric batteries having no memory effect, partial charge disadvantages or contraindications from the manufacturer, this type of battery changing from a charge enabled state to a charge disabled state with a small transition period, and not necessarily recharging to 100%. The electric battery BAT can therefore advantageously be a Lithium-Ion battery.

Of course, the invention is not limited to the embodiments described and illustrated above; one can conceive of other embodiments and other implementations without departing from the scope of the invention.

The electrical system was illustrated above in the form of an electric vehicle. However, the electrical system $V_E$ can very well be in the form of any electrical system having capacities for storing electrical energy, such as a mobile phone having a rechargeable battery.

The invention claimed is:

1. A method for the optimized recharging of an electric battery of at least one electrical system by an electrical recharging device, said at least one electrical system being an electric vehicle, the method comprising:
  determining an available charging time period between a moment when the electrical recharging device is connected to the electric battery and a moment when the electrical recharging device is disconnected from the electric battery;
  recharging the electric battery during at least one recharge interval within the available charging time period, said at least one recharge interval comprising k charging time intervals during each of which a respective charging power level is applied to recharge the electric battery;
  wherein said respective charging power is determined by:
    determining a residual electrical energy in the electric battery;
    for each of the k charging time intervals:
      sampling a load curve associated with the electrical recharging device over the available charging time period in order to obtain a set of load curve power values respectively associated with consecutive time intervals within the available charging time period;
      sorting, in ascending order, the load curve power values in order to obtain a set of sorted load curve power values;
      determining the respective charging power level of each of the k charging time intervals as a function of the residual electrical energy and of a k+1$^{th}$ load curve power value of the set of sorted load curve power values, the k charging time intervals being respectively associated with k first values of the set of sorted load curve power values.

2. The optimized recharging method according to claim 1, wherein determining the charging power levels applied during said k charging time intervals comprises the following steps, executed while an index k, starting from an initial value of 1, is incremented:
  associating, for the k time intervals associated with the k first values of the sorted load curve power values, a load curve power value at rank k that is equal to the k+1$^{th}$ load curve power value of the set of sorted load curve power values;
  calculating, for each of the k time intervals associated with the k first values of the set of sorted load curve power values, a charging power level at rank k associated with said time interval, said charging power level at rank k being determined as a function of a difference between the load curve power value at rank k and the load curve power value which are associated with said time interval;
  comparing an electrical energy at rank k, determined by applying the charging power levels at rank k to the k time intervals with which they are respectively associated, with an electrical energy required to recharge the battery;
  incrementing the index k if the electrical energy at rank k is less than or equal to the energy required to recharge the battery.

3. The optimized recharging method according to claim 2, wherein, for each of the k time intervals associated with the k first values of the sorted load curve power values, the charging power level at rank k associated with said time interval is equal to a minimum value between, on the one hand, a maximum load curve power value, and on the other hand, a difference between the load curve power value at rank k and the load curve power value which are associated with said time interval.

4. The optimized recharging method according to claim 2, wherein, when the electrical energy at rank k is greater than the energy required to recharge the battery, for each of the k time intervals associated with the k first values of the sorted load curve power values, the charging power level at rank k associated with said time interval is equal to a minimum value between, on the one hand, a maximum load curve power value, and on the other hand, a sum of the charging power level at rank k−1 and of a difference between the energy required and the electrical energy at rank k−1 divided by the number k.

5. The optimized recharging method according to claim 2, wherein, when the electrical energy at rank k is less than or equal to the energy required to recharge the battery, said determining the charging power levels further comprises comparing a charging duration at rank k, equal to a sum of the k time intervals associated with the k first values of the sorted load curve power values, and a duration of the available charging time period, the index k only being incremented if the charging duration at rank k is less than or equal to the duration of the available charging time period.

6. The optimized recharging method according to claim 5, wherein, when the charging duration at rank k is greater than the duration of the available charging time period and when the electrical energy at rank k differs from the energy required to recharge the battery by at least a predetermined difference, said determining the charging power levels includes calculating, for each consecutive time interval of the available time period, a charging power level to be applied which is equal to a minimum value between, on the one hand, a maximum load curve power value, and on the other hand, a sum of the power level at rank k associated with said time interval and a difference between the electrical energy at rank k and the required energy divided by the number k.

7. The optimized recharging method according to claim 1, wherein the recharging of the electric battery further comprises, for each of the charging time intervals with which a charging power level is associated, comparing a limit capacity level associated with said charging time interval and an estimated increased load curve power value equal to a sum of the load curve power value and of the charging power level which are associated with said charging time interval, the charging power level only being applied, during said charging time interval, if said estimated increased load curve power value is less than a limit capacity level associated with said charging time interval.

8. The optimized recharging method according to claim 7, wherein, for each charging time interval for which the estimated increased load curve power value is greater than or equal to the limit capacity level associated with said charging time interval, said each charging time interval is associated with a charging power value substantially equal to a difference between the limit capacity level and the load curve power value which are associated with said charging time interval.

9. The optimized recharging method according to claim 1, wherein the available charging time period is determined as a function of the moment when the electric battery recharging system is connected to the electrical recharging device and of an indication concerning a charging end time provided by a user of the electric vehicle.

10. The optimized recharging method according to claim 1, further comprising, prior to recharging the electric battery, verifying that the available charging time period has a duration sufficient for fully recharging the electric battery, and said recharging of the electric battery during said at least one charging time interval occurs only if the duration of the available charging time period is greater than a length of time required for fully recharging the electric battery.

11. The optimized recharging method according to claim 1, wherein the electric battery is to be modulated in charging power and has substantially no memory effect.

12. A non-transitory computer readable storage medium, having stored thereon a computer program comprising program instructions, the computer program being loadable into a data-processing unit and adapted to cause the data-processing unit to carry out the steps of claim 1 when the computer program is run by the data-processing unit.

13. An optimized recharging device for recharging at least one electric vehicle, connected to an electrical grid and comprising at least one connection port suitable for connection to the electric battery of an electric vehicle, the device being configured to implement the steps of the method according to claim 1 after the electric battery of an electric vehicle is connected to the connection port of the optimized recharging device.

14. An optimized recharging system for electrically recharging a fleet composed of at least one electric vehicle, the system comprising an electrical grid and the electrical recharging device according to claim 13, connected to said electrical grid.

15. The optimized recharging system according to claim 14, further comprising a remote computer system, connected to the optimized recharging device and comprising a processing unit suitable for carrying out the steps of the method according to claim 1.

* * * * *